(12) United States Patent
Kube

(10) Patent No.: US 8,506,585 B2
(45) Date of Patent: Aug. 13, 2013

(54) INSERTION SYSTEM AND INSERTION DEVICE

(75) Inventor: Oliver Kube, Worms (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 230 days.

(21) Appl. No.: 13/168,197

(22) Filed: Jun. 24, 2011

(65) Prior Publication Data
US 2012/0022344 A1 Jan. 26, 2012

Related U.S. Application Data

(63) Continuation of application No. PCT/EP2009/008226, filed on Nov. 19, 2009.

(30) Foreign Application Priority Data

Dec. 24, 2008 (EP) ..................................... 08022458

(51) Int. Cl.
*A61B 17/32* (2006.01)
(52) U.S. Cl.
USPC .......................................... 606/167; 606/181

(58) Field of Classification Search
USPC .................... 606/167, 181–189; 604/164.01, 604/196, 220, 272
See application file for complete search history.

(56) References Cited

U.S. PATENT DOCUMENTS 7,901,382 B2 *   3/2011   Daily et al. ................... 604/187
2004/0158207 A1   8/2004   Hunn

FOREIGN PATENT DOCUMENTS

| WO | WO 2006/061354 | 6/2006 |
| WO | WO 2008/065646 | 6/2008 |
| WO | WO 2008/078318 | 7/2008 |

* cited by examiner

*Primary Examiner* — Gregory Anderson
(74) *Attorney, Agent, or Firm* — Harness, Dickey

(57) ABSTRACT

An insertion system having a base unit for placing on the body of a patient and an insertion device that can be coupled to the base unit, wherein the insertion device comprises an insertion needle holder for holding an insertion needle and a drive mechanism for displacing the insertion needle holder in a pricking direction. According to the invention, the insertion device comprises a locking mechanism causing locking of the drive mechanism in an active state and being set to an inactive state in which the locking is released by coupling the insertion device to the base unit.

13 Claims, 6 Drawing Sheets

INSERTION SYSTEM AND INSERTION DEVICE

CROSS-REFERENCE TO RELATED APPLICATIONS

This application is a continuation of International Patent Application No. PCT/EP2009/008226, filed Nov. 19, 2009, which claims the benefit and priority of EP 08022458.7, filed Dec. 24, 2008. The entire disclosures of the above applications are incorporated herein by reference.

BACKGROUND

The invention relates to a system for inserting a sensor for measuring an analyte, e.g., glucose, under in vivo conditions, and a corresponding insertion device.

In order to insert sensors for measuring analyte concentrations under in-vivo conditions, for example, glucose concentrations, in body tissue of a patient, for example, in subcutaneous fatty tissue, it is customary to use insertion devices that effect a puncturing motion of an insertion needle by means of a drive mechanism. Customary insertion needles for this purpose are designed as hollow needles or V-shaped trough, in which a sensor is situated. The sensor can, for example, be provided as an electrode system for electrochemical measurements or comprise a micro-fluidic catheter for guiding a perfusion fluid in and out. After a puncture is made, the insertion needle is retracted from the body tissue, whereby the sensor remains in the puncturing wound thus generated.

Another application of insertion devices is, for example, the application of catheters, in particular for infusion of insulin or other active substances.

Combined with a base unit to which they can be coupled for an insertion, insertion devices of this type form an insertion system. It is customary to glue base units to the body of a patient. Subsequently, an insertion device can be coupled to the base unit. After the insertion is completed, the insertion device can be un-coupled from the base unit such that the base unit remains on the body of the patient, for example, as carrier or connection element of an inserted sensor or catheter.

Insertion systems are often operated by the patients themselves, for example, in order to insert catheters for connection to an insulin pump or sensors for measuring the glucose concentration. Therefore, it is a steady aim in the development of such insertion systems that they can be operated as easily and safely as feasible.

This object is met by an insertion system and insertion device having the features described herein.

SUMMARY

According to the invention, the insertion device includes a locking mechanism which, in an active state, effects locking of the drive mechanism and is transitioned to an inactive state, in which the locking is released, by coupling the insertion device to the base unit. A locking mechanism of this type, which locks the drive mechanism in its active state, can be used to prevent premature triggering of a puncture and thus reduce the risk of injury while handling the insertion device.

In an insertion device according to the invention, the locking mechanism unlocks automatically upon coupling of the insertion device to the base unit. Accordingly, what can be attained according to the invention is that the locking mechanism is unlocked only when the insertion device is coupled to the base unit. What can therefore be advantageously attained is that a user can unlock the locking mechanism only by coupling the insertion device to the base unit. Advantageously, a puncturing can therefore be triggered only when the insertion device is coupled to the base unit such that the risk of injury due to incorrect handling is largely excluded.

Aside from increased safety from injuries, another advantage of the locking mechanism according to the invention is that the operation of the insertion device can be simplified significantly. Whereas known insertion devices usually use more or less laborious and complicated triggering or actuation mechanisms to prevent inadvertent triggering of a puncture, for example, by means of providing multiple actuation elements that need to be actuated in a given order or combination, measures of this type are dispensable in the insertion system according to the invention. Since the drive mechanism can effect a puncture only after coupling of the insertion device to the base unit, premature triggering of a puncture is excluded even upon the use of the simplest triggering and actuation mechanisms.

A securing mechanism according to the invention can, for example, be transitioned from its active state to its inactive state by means of magnetic force. Magnets required for this purpose can be attached to the base unit and/or the insertion device. It is feasible just as well to deactivate the securing mechanism by electrical means by closing an electrical contact while coupling the insertion device to the base unit. However, it is preferable for the securing mechanism to operate by purely mechanical means, for example, by providing on the base unit an index pin that actuates the securing mechanism during the coupling process and thus transitions it to the inactive state.

A locking mechanism according to the invention can, for example, operate with a safety catch, a rocker or a similar locking element that is transitioned from a locked state to an inactive state by means of a rotating or swinging motion. However, it is preferable for the locking mechanism to include a slider that is displaced during a switch of the locking mechanism from the active state to the inactive state. A slider of this type can, for example, carry a locking element that blocks the drive mechanism, in particular by means of a positive fit-type engagement.

It is also feasible for the slider, which is preferably present in a locking mechanism according to the invention, to itself lock the drive mechanism as a locking element by means of form-fitting engagement in the drive mechanism or in an actuation element that can be actuated by a user. Basically, a slider of this type might be displaced in an arbitrary direction upon a switch of the locking mechanism from the active state to the inactive state. However, preferably, the slider can be displaced in the puncturing direction since this facilitates a compact design.

An advantageous refinement of the invention provides the slider to be subjected to the action of a spring. In this context, any component that generates a restoring force upon deformation can be used as spring. For example, a plastic block capable of elastic deformation, a coil made of plastic or metal, and a band capable of elastic deformation, for example, a rubber band, can be used as spring. What can be attained by means of the use of a slider subjected to the action of a spring is that said slider is moved to a starting or final position by means of spring force. Accordingly, the risk of the slider remaining in an undefined intermediary state between the starting and the final position for extended periods of time can, therefore, be reduced. Preferably, the spring relaxes when the locking mechanism switches to the inactive state, i.e., releases at least a fraction of the energy that is stored in it. This measure is advantageous in that a user does not need to expend additional force for deactivation of the locking mechanism. Moreover, a particularly simple design of the locking mechanism can be attained in this manner, since it suffices to block any displacement of the slider in the active state of the locking mechanism by means of a mobile element, for example, a limit stop or barrier. Upon coupling the insertion device to a base unit, an element of this type can be moved by means of contact to a matching component of the base unit and a displacement of the slider can thus be facilitated.

Preferably, the slider is coupled to a latching element that is slid into an engagement position when the insertion device is coupled to the base unit, in which engagement position it connects the insertion device to the base unit in a positive fit-type manner. What can be attained in this manner is that the locking mechanism transitions to its inactive state only once the insertion device is connected to the base unit in a positive fit-type, and therefore reliable, manner.

Preferably, the locking mechanism includes a protection element which, in the active state of the locking mechanism, is situated in front (in the direction of puncturing) of an insertion needle that is held by the insertion needle holder. This measure is advantageous in that the insertion needle is covered and thus the risk of injury during any handling of the insertion device is further reduced. A protection element of this type can, for example, be connected to the above-mentioned slider, in particular connected by a joint, such that it is pushed aside during transition of the locking mechanism to the inactivate state such that the path for a puncturing motion of the insertion needle is thus freed. The protection element, which can, for example, be provided to be plate-shaped, can advantageously be connected to the above-mentioned latching element, in particular provided as a single part that also includes the latching element, which effects a positive fit with the base unit when the insertion device is coupled.

The drive mechanism of an insertion device according to the invention can contain an energy storage device, for example, a spring, in order to supply the energy required for a puncturing motion. However, it is also feasible for the drive mechanism of the insertion device according to the invention, in operation, to convert a drive motion of an actuating element into a puncturing motion of the insertion needle holder. In this context, it is preferred for the drive mechanism to effect a returning motion of the insertion needle holder subsequent to a puncturing motion, and to be blocked after the returning motion is completed. Said blockade can be effected by the locking mechanism also or by a mechanism that is independent thereof. It is feasible, for example, that an actuating element whose drive motion is converted into a puncturing motion by the drive mechanism to snap into place at the end of its actuation path.

DRAWINGS

Further details and advantages of the invention are described by means of exemplary embodiments making reference to the appended drawings. In this context, identical and corresponding components are labeled with consistent reference numbers.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
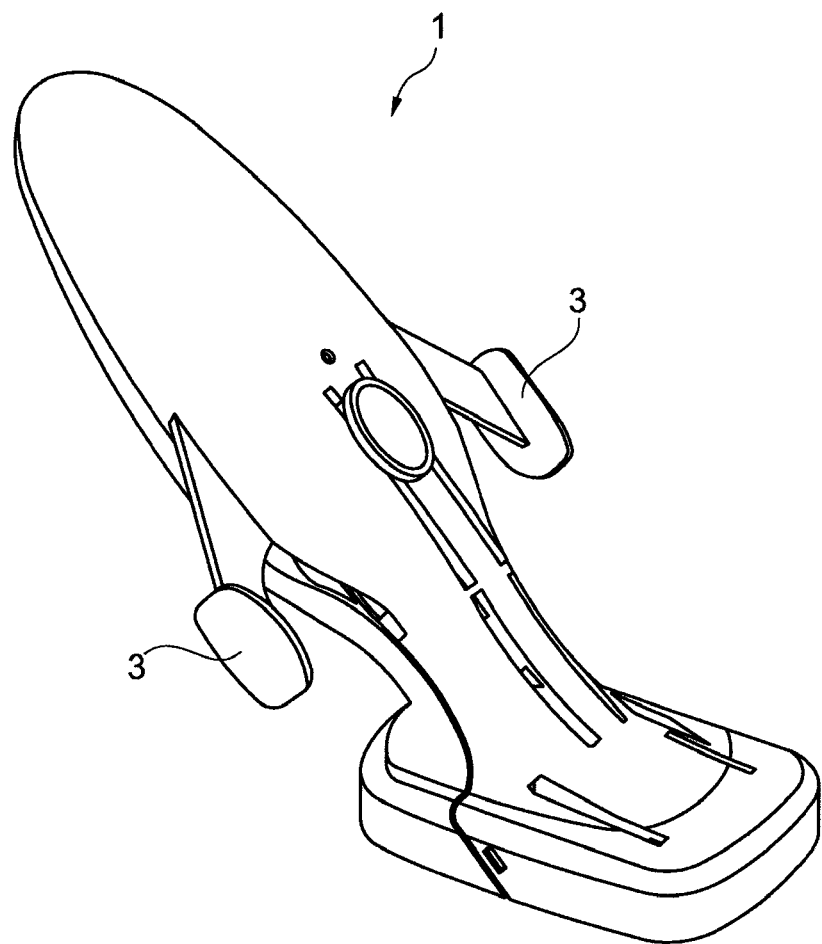
FIG. 1 shows an embodiment of an insertion device according to the invention.
Figure 2:
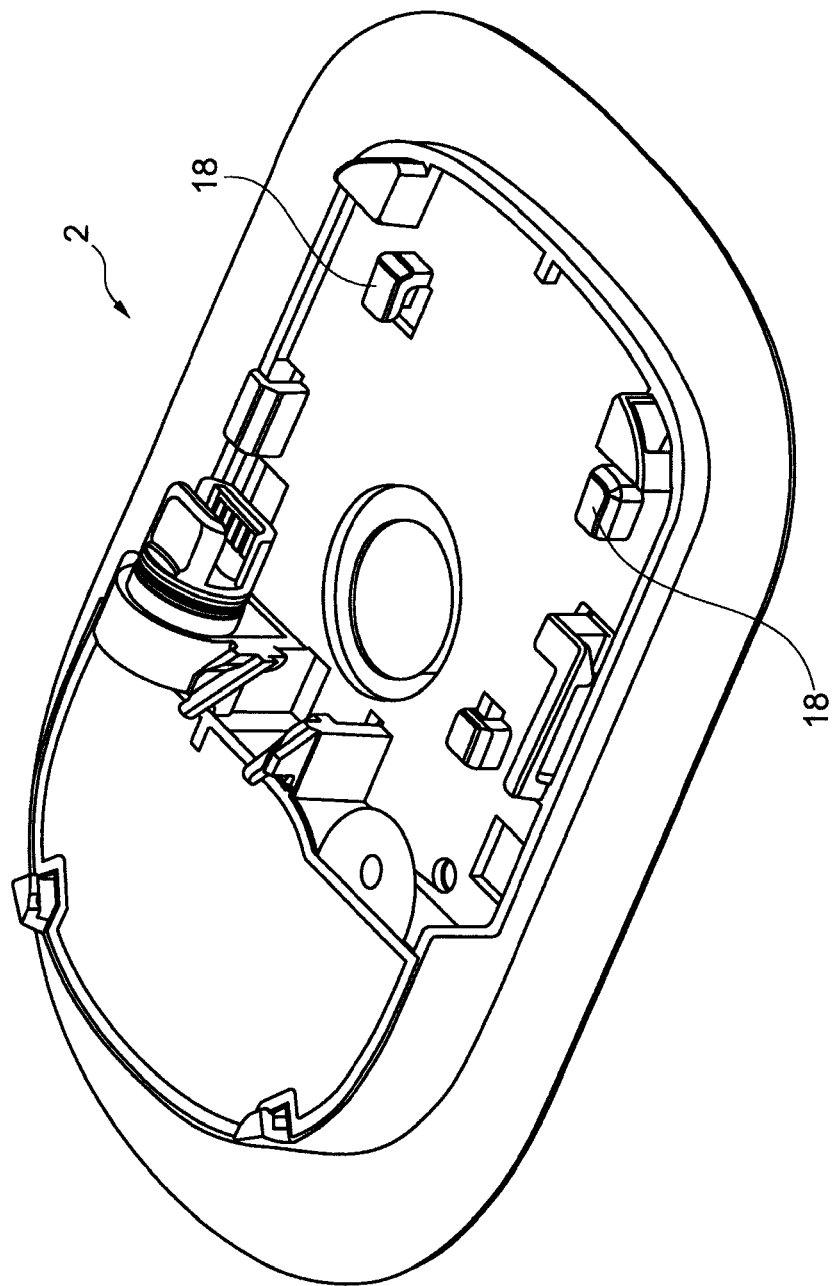
FIG. 2 shows an embodiment of a corresponding base unit.

The insertion device 1 shown in FIG. 1 and the base unit 2 shown in FIG. 2 jointly form an insertion system that can be used, for example, to insert sensors by means of insertion needles or catheters for the infusion of insulin or other active substances into the body of a patient. For insertion, the bottom side of the base unit 2 is glued to the body of a patient and then the insertion device 1 is coupled to the base unit 2.

The insertion device 1 shown in FIG. 1 has two actuating elements 3, which are moved towards each other in a drive motion for an insertion. Said drive motion is converted into a puncturing motion of an insertion needle holder and thus of an insertion needle by a drive mechanism that is shown in FIGS. 3 to 6.

Figure 3:
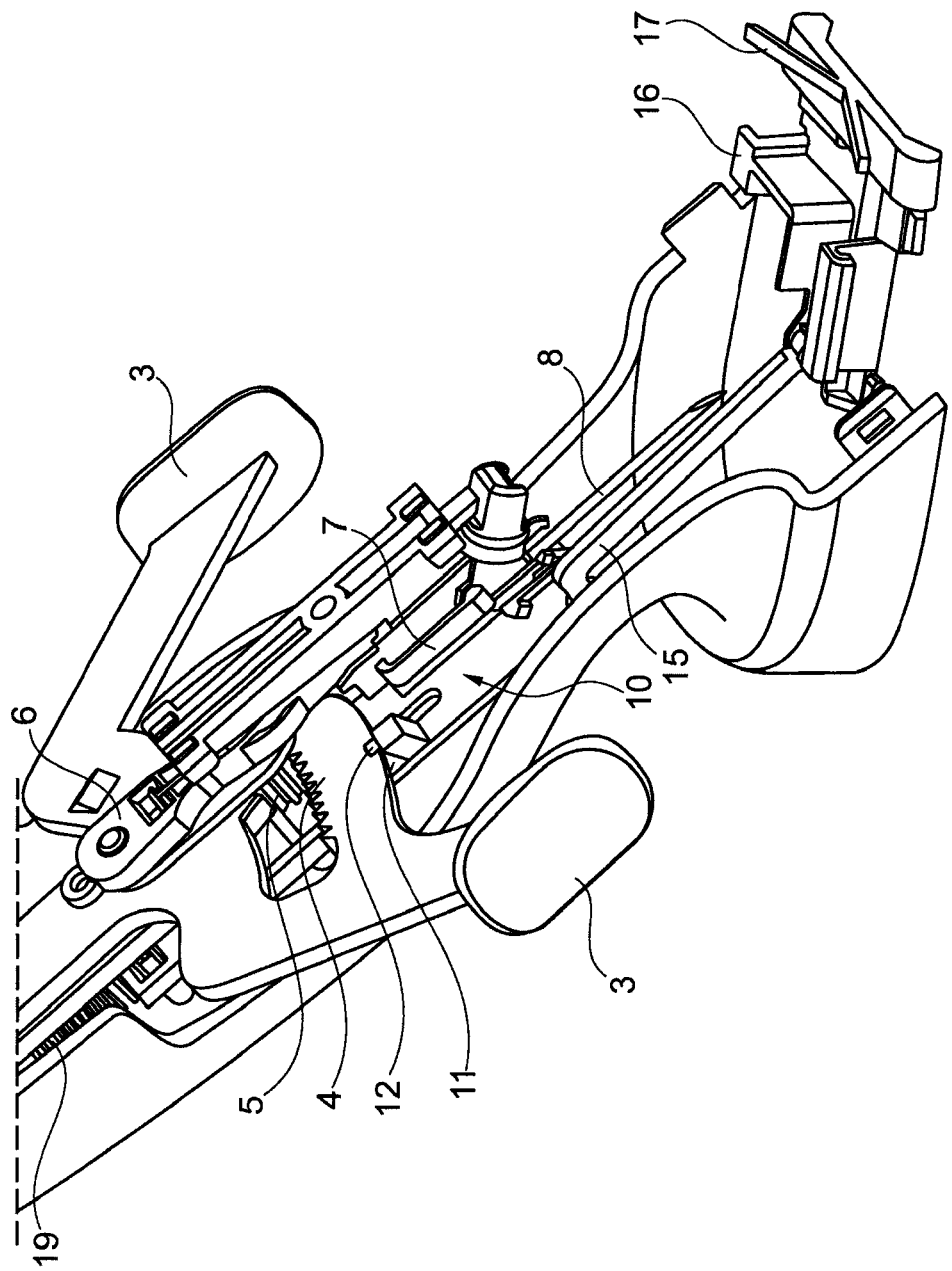
FIG. 3 shows a detail of the insertion device shown in FIG. 1 with its housing being open.
Figure 4:
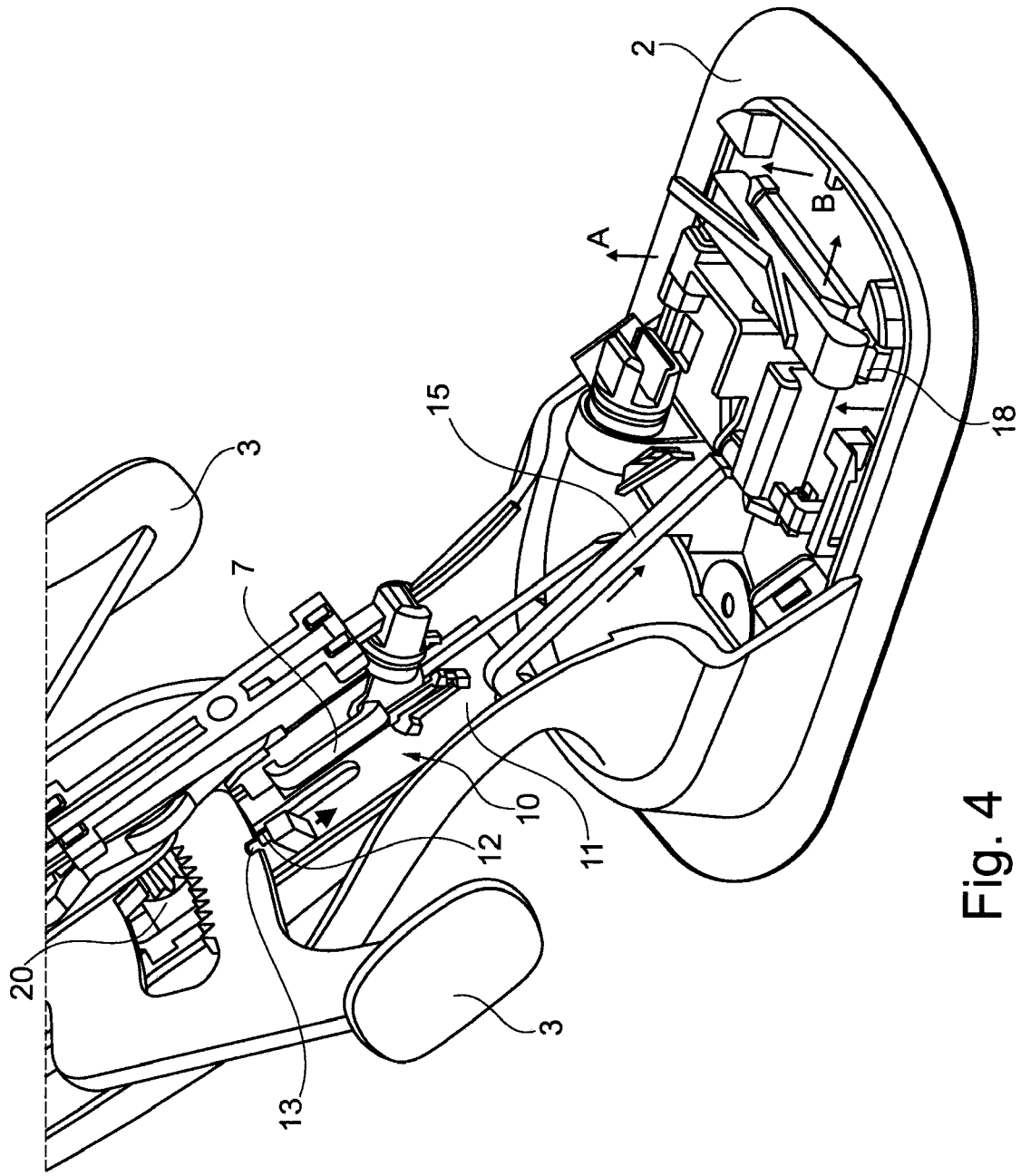
FIG. 4 shows a view according to FIG. 3 with the base unit being coupled.

As shown in FIG. 3, the actuating elements 3 are provided with toothed racks 4, which cause a rotor 5 to rotate when the two actuating elements 3 are squeezed together, whereby the rotation is converted via a connecting rod 6 into a linear puncturing motion of an insertion needle holder 7 and of an insertion needle 8 carried by the holder. The toothed racks 4, the rotor 5, and the connecting rod 6 jointly form the drive mechanism of the insertion device 1.

In order to counteract a risk of injury due to a premature puncturing motion, the insertion device 1 has a locking mechanism 10, which, in an active state, effects a locking of the drive mechanism, i.e., blocks its motion, and is transitioned to an inactive state, in which the locking is released, by coupling the insertion device 1 to the base unit 2.

In the embodiment shown in FIG. 3, the locking mechanism 10 includes a slider 11 that carries a locking element 12, which, in the active state shown in FIG. 3, engages a recess 13 of one of the actuating elements 3 and thus blocks the drive mechanism. The slider 11 is connected by a joint by means of an arm 15 to a latching element 16 that is pushed into an engagement position upon coupling the insertion device 1 to the base unit 2, and connects the insertion device 1 to the base unit 2 in a positive fit-type manner in said engagement position. In the active state of the locking mechanism shown in FIG. 3, displacement of the latching element 16 is prevented by means of a blockade element 17.

Upon coupling the insertion device 1 to the base unit 2, the blockade element 17 is moved by the base unit 2 transverse to the direction, in which the latching element 16 is displaced, i.e., it is lifted in the embodiment shown, and thus a displacement path for the latching element 16 leading towards the engagement position is released. By means of a subsequent displacement motion, the latching element 16 engages the base unit 2, namely by being slid under engagement elements 18 that are provided for this purpose and are evident, in particular, in FIGS. 2 and 4.

Said displacement motion is effected by a spring 19 that is shown in FIG. 3, which spring 19 is provided as a coiled spring in the embodiment shown, preferably made of plastic, and presses onto the slider 11. The spring 19 relaxes when the locking mechanism 11 transitions from the active state shown in FIG. 3 to its inactive state shown in FIG. 4. In the process, the spring 19 displaces the slider 11 in the puncturing direction. Said displacement motion is transferred by means of the jointed arm 15 to the latching element 16, which is thus made to move into its engagement position in the base unit 2.

Figure 5:
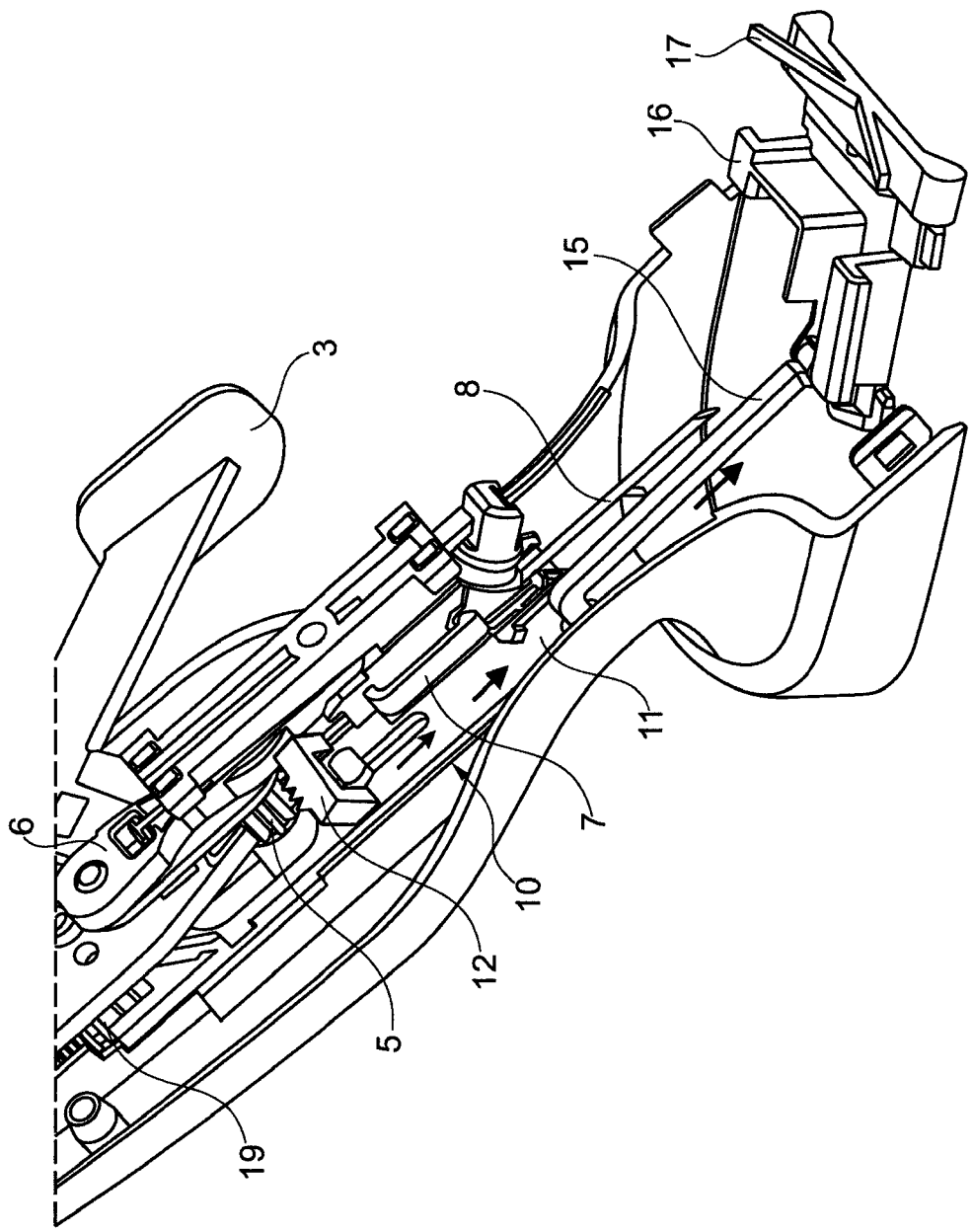
FIG. 5 shows a detail of another embodiment of an insertion device with its housing being open.
Figure 6:
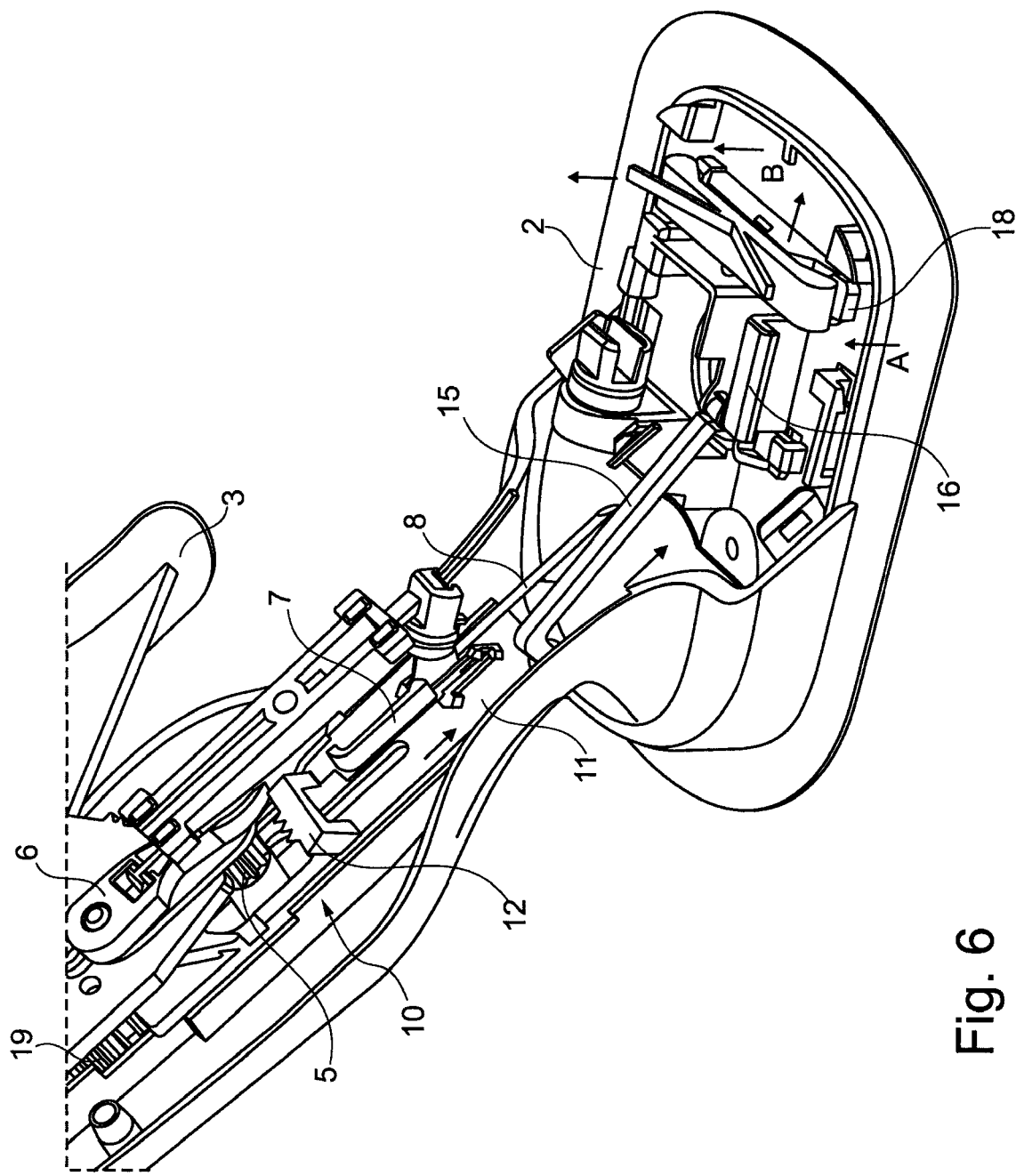
FIG. 6 shows a view according to FIG. 5 with base unit coupled.

FIGS. 5 and 6 show another embodiment, which differs from the embodiment described above essentially only in that, in the active state of the locking mechanism 10 shown in FIG. 5, a locking element 12 that is carried by the slider 11 engages the rotor 5 of the drive mechanism, which rotor is provided in the form of a cogwheel, and thus blocks the rotor 5. The locking mechanism transitions to the inactive state shown in FIG. 6 by displacement of the slider 11 in the puncturing direction.

In both embodiments, a risk of injury upon handling of the insertion device 1 is reduced additionally in that, in the active state of the locking mechanism, a component of the locking mechanism 10 is situated in front (in puncturing direction) of an insertion needle 8 that is held by the insertion needle holder 7. In the embodiments shown, said component acting as a protection element is a shift plate which simultaneously forms the latching element 16. Upon transition of the locking mechanism 10 to its inactive state, the latching element 16 is displaced such that the insertion needle 8 is moved through an orifice that is provided in the floor of the base unit 2 and can thus be punctured into the body of a patient.

The slider 11 of the locking mechanism 10 can be displaced in the puncturing direction and is provided with a linear guidance in each of the two embodiments. In the embodiments shown, the linear guidance is provided in the form of a slit in the slider 11 through which reaches a guiding element 20 of the housing.

The actuating elements 3 can snap into a latching mechanism (not shown) at the end of a drive motion to prevent any inadvertent puncturing motion, which may lead to an injury, after uncoupling of an insertion device 1 from the base unit 2, i.e., after an insertion.

Subsequent to a puncturing motion, the drive mechanism effects a returning motion of the insertion needle holder 7. Preferably, the coupling between insertion device 1 and base unit 2 is released again by said returning motion. This can be attained, for example, in that the slider 11 couples to and is pulled backwards by the insertion needle holder 7 during the returning motion. The slider 11 can, for example, carry a leaf spring in an inclined orientation that is bent by the insertion needle holder during the puncturing motion such that the insertion needle holder 7 can slide over the slider 11. During the returning motion, a leaf spring of this type can engage the insertion needle holder 7 such that the slider 11 is pulled back by the insertion needle holder 7 and thus, via the arm 15, the latching element 16 is also pulled from its position of engagement to the base unit 2.

LIST OF REFERENCE NUMBERS

1 Insertion device
2 Base unit
3 Actuating element
4 Toothed rack
5 Rotor
6 Connecting rod
7 Insertion needle holder
8 Insertion needle
9
10 Locking mechanism
11 Slider
12 Locking element
13 Recess
14
15 Arm
16 Latching element
17 Blockade element
18 Engagement element
19 Spring
20 Guiding element

What is claimed is:

1. An insertion system comprising a base unit for placing on the body of a patient and an insertion device that can be coupled to the base unit, whereby the insertion device comprises:
   an insertion needle holder for holding an insertion needle;
   a drive mechanism for moving the insertion needle holder in a puncturing direction; and
   a locking mechanism that effects locking of the drive mechanism in an active state and is transitioned to an inactive state, in which the locking is released, by coupling the insertion device to the base unit; wherein the locking mechanism comprises a slider that is displaced from the active state to the inactive state upon a switch of the locking mechanism, the slider being coupled to a latching element that is slid into an engagement position when the insertion device is coupled to the base unit, in which engagement position it connects the insertion device to the base unit in a positive fit-type manner.

2. An insertion device for an insertion system having a base unit for placing on the body of a patient, the insertion device comprising:
   an insertion needle holder for holding an insertion needle;
   a drive mechanism for moving the insertion needle holder in a puncturing direction; and
   a locking mechanism that effects locking of the drive mechanism in an active state and is transitioned to an inactive state, in which the locking is released, by coupling the insertion device to the base unit; wherein the locking mechanism comprises a slider that is displaced from the active state to the inactive state upon a switch of the locking mechanism, the slider being coupled to a latching element that is slid into an engagement position when the insertion device is coupled to the base unit, in which engagement position it connects the insertion device to the base unit in a positive fit-type manner.

3. The insertion device according to claim 2, characterized in that the slider can be displaced in the puncturing direction.

4. The insertion device according to claim 2, characterized in that the slider is subjected to the action of a spring.

5. The insertion device according to claim 2, characterized in that the spring relaxes upon a switch of the locking mechanism to the inactive state.

6. The insertion device according to claim 2, further comprising a blockade element that blocks a displacement of the latching element in the active state of the locking mechanism.

7. The insertion device according to claim 6, characterized in that the blockade element is moved transverse to the direction, in which the latching element is displaced, when the insertion device is coupled to the base unit, and thus a displacement path leading towards the engagement position is released for the latching element.

8. The insertion device according to claim 2, characterized in that the slider is coupled to the latching element by means of an articulated joint.

9. The insertion device according to claim 2, characterized in that the locking mechanism, in the active state, blocks an actuating element of the drive mechanism.

10. The insertion device according to claim 9, characterized in that the drive mechanism, in operation, converts a drive motion of the actuating element into a puncturing motion of the insertion needle holder.

11. The insertion device according to claim 2, characterized by a linear guidance for the slider.

12. The insertion device according to claim 2, characterized in that the drive mechanism effects a returning motion of the insertion needle holder subsequent to a puncturing motion, and is blocked after the returning motion is completed.

13. The insertion device according to claim 2, characterized in that the locking element includes a protection element which, in the active state of the locking mechanism, is situated in front of an insertion needle that is held by the insertion needle holder.

* * * * *